(12) United States Patent
Bayer et al.

(10) Patent No.: US 11,850,402 B2
(45) Date of Patent: Dec. 26, 2023

(54) AUTOMATIC INJECTION DEVICE WITH REUSABLE PORTION

(71) Applicant: Eli Lilly and Company, Indianapolis, IN (US)

(72) Inventors: Kelsey Christine Bayer, Indianapolis, IN (US); Julia Kay Jacob, Indianapolis, IN (US); Leema Maria John, Burnsville, MN (US); Mehul Sanmukh Patel, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 25 days.

(21) Appl. No.: 18/004,214

(22) PCT Filed: Jul. 1, 2021

(86) PCT No.: PCT/US2021/040041
§ 371 (c)(1),
(2) Date: Jan. 4, 2023

(87) PCT Pub. No.: WO2022/010726
PCT Pub. Date: Jan. 13, 2022

(65) Prior Publication Data
US 2023/0191032 A1 Jun. 22, 2023

Related U.S. Application Data

(60) Provisional application No. 63/049,724, filed on Jul. 9, 2020.

(51) Int. Cl.
*A61M 5/28* (2006.01)
*A61M 5/315* (2006.01)
*A61M 5/32* (2006.01)

(52) U.S. Cl.
CPC ........ *A61M 5/285* (2013.01); *A61M 5/31578* (2013.01); *A61M 5/321* (2013.01)

(58) Field of Classification Search
CPC ... A61M 5/321; A61M 5/31578; A61M 5/285
See application file for complete search history.

(56) References Cited

U.S. PATENT DOCUMENTS 7,556,623 B2  7/2009 Lyman et al.
8,568,141 B2  10/2013 Tanaka et al.
(Continued)

FOREIGN PATENT DOCUMENTS

WO  2011131782  10/2011
WO  2011139110  11/2011
(Continued)

OTHER PUBLICATIONS

Patent Cooperation Treaty International Search Report of the International Searching Authority pertaining to International Application No. PCT/US2021/040041; International Filing Date: Jul. 1, 2021; dated Oct. 15, 2021.

(Continued)

*Primary Examiner* — Tasnim Mehjabin Ahmed
(74) *Attorney, Agent, or Firm* — M. Daniel Spillman

(57) ABSTRACT

An autoinjector may include a disposable portion and a reusable portion. The disposable portion may include a syringe and a syringe coupling. The syringe coupling may be coupled to the syringe, and may comprise a guide track. The reusable portion may include a device housing, a device actuator configured to initiate an injection of the autoinjector, and a motor coupled to the device actuator. The reusable portion may additionally include a motor foot coupled to an output of the motor, wherein the motor foot may be configured to translate in an axial direction. The reusable portion may also include a drive coupling disposed within the device (Continued)

housing. The drive coupling may include an angled surface configured to receive the motor foot and a protrusion configured to engage with the guide track of the syringe coupling to lock the drive coupling to the syringe coupling.

13 Claims, 8 Drawing Sheets

(56) References Cited

U.S. PATENT DOCUMENTS

| | | |
|---|---|---|
| 8,900,202 B2 | 12/2014 | Helmer et al. |
| 9,452,261 B2 | 9/2016 | Alon |
| 9,623,183 B2 | 4/2017 | Jennings et al. |
| 9,835,279 B2 | 12/2017 | Plumptre et al. |
| 10,384,007 B2 | 8/2019 | Henderson et al. |
| 2006/0173439 A1 | 8/2006 | Thorne et al. |
| 2012/0233834 A1 | 9/2012 | Szechinski et al. |
| 2013/0090602 A1* | 4/2013 | Avery .............. A61M 5/24 604/189 |
| 2014/0039405 A1 | 2/2014 | Konandreas et al. |
| 2014/0330215 A1 | 11/2014 | Kikuchi et al. |
| 2016/0193412 A1* | 7/2016 | Cereda ............ A61M 5/36 604/125 |
| 2017/0274150 A1 | 9/2017 | Takabatake et al. |
| 2018/0140461 A1 | 5/2018 | Nandigala et al. |
| 2019/0381240 A1 | 12/2019 | Novickoff et al. |

FOREIGN PATENT DOCUMENTS

| | | | |
|---|---|---|---|
| WO | WO-2011139110 A2 * | 11/2011 | ............ A61M 5/168 |
| WO | 2019158372 | 8/2019 | |

OTHER PUBLICATIONS

Patent Cooperation Treaty Written Opinion of the International Searching Authority pertaining to International Application No. PCT/US2021/040041; International Filing Date: Jul. 1, 2021; dated Oct. 15, 2021.

* cited by examiner

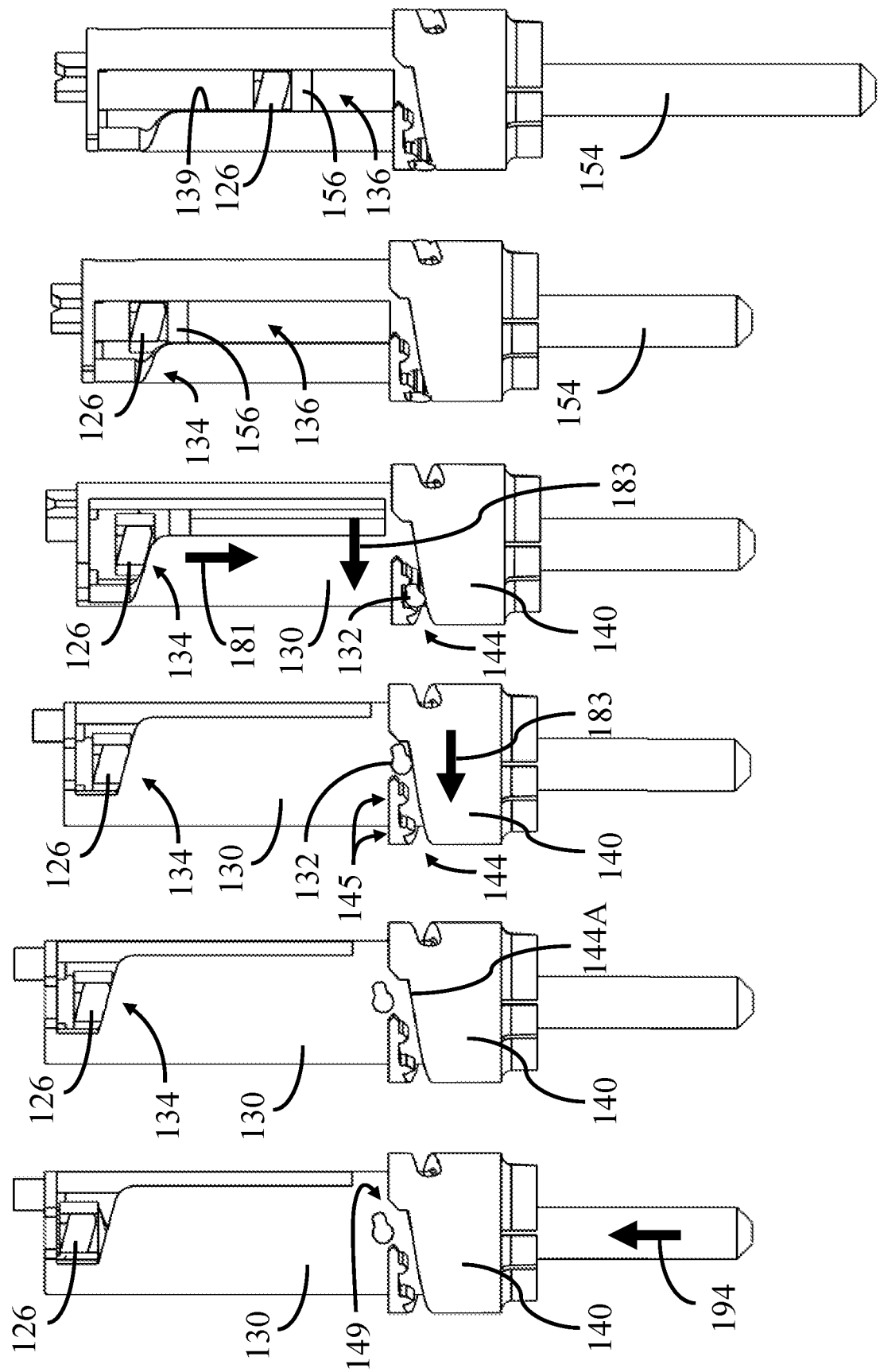

AUTOMATIC INJECTION DEVICE WITH REUSABLE PORTION

FIELD

Disclosed embodiments are related to automatic injection devices and related methods.

BACKGROUND

Patients suffering from a number of different diseases often inject themselves with pharmaceuticals. A variety of devices have been proposed to facilitate these injections. One type of device is an automatic injection device, or autoinjector. This type of device typically includes a trigger assembly that, when operated by a user, causes the device to automatically insert into the user a needle of a syringe. After insertion of the needle, the device may automatically inject a dose of medication through the needle into the user.

SUMMARY

In some embodiments, an assembly of an autoinjector includes a syringe and a syringe coupling. The syringe includes a body with an internal cavity, a moveable seal at least partially disposed within the internal cavity of the body, and a needle coupled to a distal portion of the body. The syringe coupling is coupled to the body of the syringe and includes a guide track configured to receive a protrusion of a drive coupling to lock the syringe coupling to the drive coupling.

In some embodiments, an assembly of an autoinjector includes a device housing, a device actuator configured to initiate an injection of the autoinjector, and a motor coupled to the device actuator. The assembly additionally includes a motor foot coupled to an output of the motor, wherein the motor foot is configured to translate in an axial direction. The assembly also includes a drive coupling disposed within the device housing. The drive coupling includes an angled surface configured to receive the motor foot, and a protrusion configured to engage with a guide track of a syringe coupling to lock the drive coupling to the syringe coupling.

In some embodiments, a method of operating an autoinjector includes translating a motor foot coupled to an output of a motor in a distal direction to cause the motor foot to contact a drive coupling, thereby translating the drive coupling in the distal direction to cause the drive coupling to contact a syringe coupling. The method further includes rotating the drive coupling relative to the syringe coupling, thereby locking the drive coupling to the syringe coupling, and translating the drive coupling and syringe coupling together in the distal direction, thereby deploying a needle of a syringe associated with the syringe coupling. The method additionally includes translating the motor foot relative to the drive coupling in the distal direction to cause the motor foot to displace a moveable seal of the syringe, thereby delivering a material disposed within the syringe through the needle.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 6A depicts a motor foot translating in a distal direction;

FIG. 6B depicts a motor foot contacting a drive coupling;

FIG. 6C depicts a motor foot and a drive coupling translating in a distal direction;

FIG. 6D depicts a drive coupling rotating relative to a syringe coupling;

FIG. 6E depicts a motor foot contacting a plunger;

FIG. 6F depicts a motor foot depressing a plunger;

DETAILED DESCRIPTION

Figure 1:
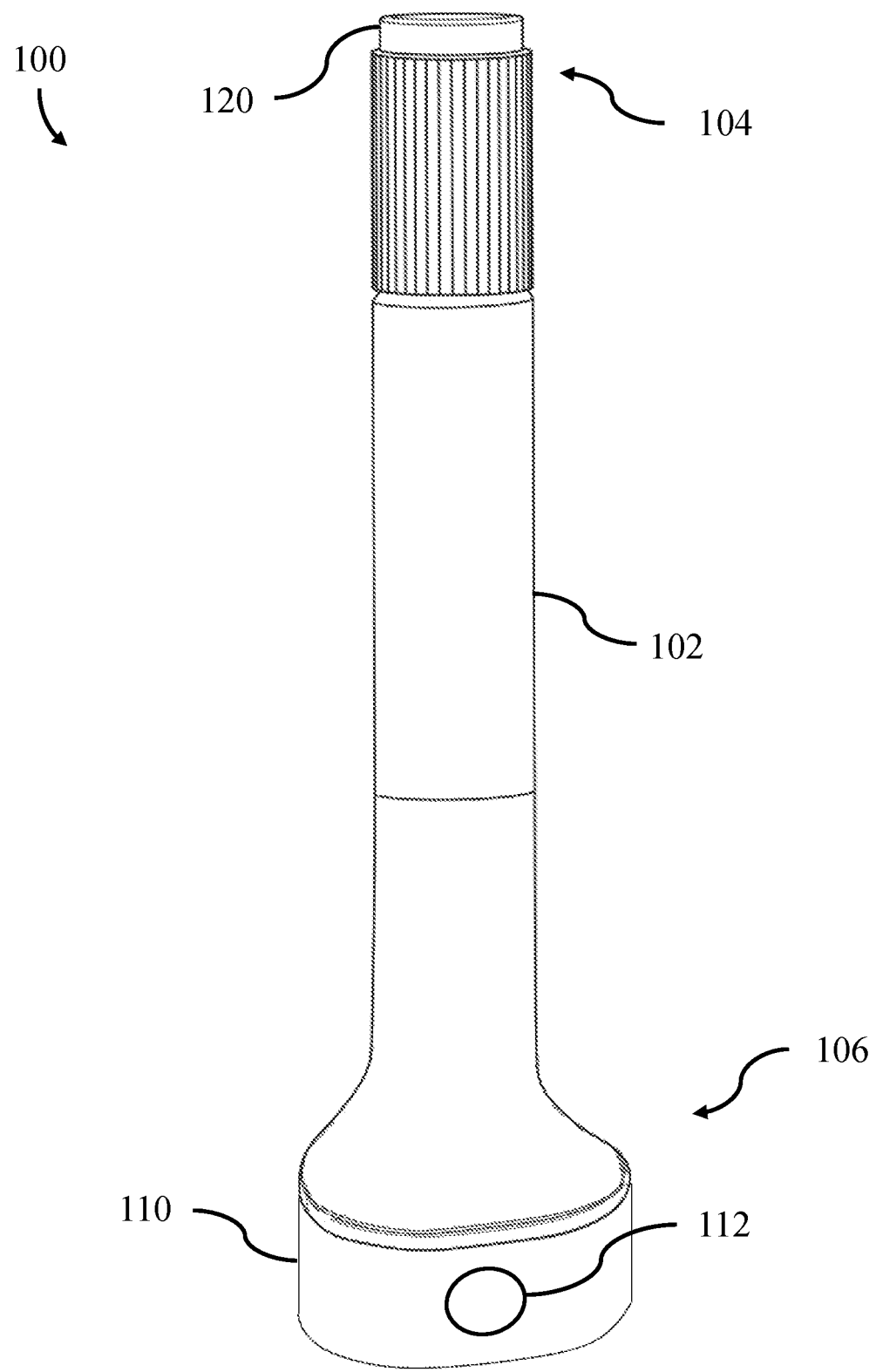
FIG. 1 is a perspective view of one embodiment of an autoinjector.

A conventional autoinjector is often intended to be disposed of in its entirety after the medication contained within the autoinjector has been delivered. While the inventors have appreciated that a disposable autoinjector may provide certain benefits, the inventors have also recognized and appreciated potential benefits associated with a reusable autoinjector. A reusable autoinjector may reduce waste, may be more cost-effective to the manufacturer and/or to the user in the aggregate, may enable the use of more durable materials, and may permit the inclusion of more robust functionality and/or additional features. For example, a reusable autoinjector may include sophisticated electronics, enabling a connected, smart device that may include reminders, logging of injections, and/or other automated features. While each individual autoinjector may be more expensive for a manufacturer to make and/or for a user to purchase, there may be cost savings overall, as fewer autoinjectors may need to be produced and purchased to fulfill a treatment regimen.

However, there may be challenges associated with a reusable autoinjector. At least a portion of a reusable autoinjector may still be disposable, for example due to sterility considerations. As such, a reusable autoinjector may include an interface between a reusable portion and a disposable portion. It may be desirable for a reusable autoinjector with an interface between a reusable portion and a disposable portion to retain at least the same functionality of a conventional, disposable autoinjector. For example, the drive system of an autoinjector may include capabilities related to automatic needle insertion, automatic injection of a medication, and/or automatic needle retraction. A reusable autoinjector may additionally include the capability of separating the disposable and reusable portions after injection, and/or installing a new, unused disposable portion after discarding the old, used disposable portion.

In view of the above, the inventors have recognized and appreciated the benefits of a reusable autoinjector that includes an interface between a reusable portion and a disposable portion within a drive system of the reusable autoinjector. In some embodiments, a drive system may include a plurality of components that convert motion from an output of an actuator, such as a motor, into needle insertion, drug injection (which may include depressing a plunger that displaces a moveable seal of a syringe), and/or needle retraction.

In some embodiments, a disposable portion of an autoinjector may include a syringe and a syringe coupling. To this end, a patient may receive one or more disposable portions distributed separately from the durable portion. In some instances, each of the disposable portions include the same dosage and medication. In others, at least one of the disposable portions include the same medication but with different dosages, for example, for titration. In others, at least one of the disposable portions include different medications for different treatment capabilities. The syringe may include a body with an internal cavity, a moveable seal at least partially disposed within the internal cavity of the body, and a needle coupled to a distal portion of the body. The syringe coupling may be coupled to the body of the syringe, and may be configured to engage with a drive coupling of a reusable portion of an autoinjector. In some embodiments, the syringe coupling may be rotationally fixed relative to the body of the syringe. In some embodiments, the disposable portion of an autoinjector may additionally include a base cap, which may include a syringe removal tool in some embodiments. The syringe removal tool may be configured to unlock the syringe coupling from the drive coupling, thereby separating the disposable portion of the autoinjector from the reusable portion after use.

In some embodiments, a reusable portion of an autoinjector may include a device housing, a device actuator configured to initiate an injection, and a motor coupled to the device actuator. In some embodiments, a reusable portion of an autoinjector may include a lock, wherein the lock is configured to prevent operation of the device actuator when in a locked condition and to allow operation of the device actuator when in an unlocked condition. An output of the motor may be coupled to a motor foot, which may be configured to translate in an axial direction. The reusable portion may additionally include a drive coupling configured to engage with the syringe coupling of the disposable portion. The drive coupling may include an angled surface configured to receive the motor foot, wherein the angled surface may be configured to convert translation of the motor foot into rotation of the drive coupling. When the motor foot contacts the angled surface of the drive coupling, an axial displacement of the motor foot in a distal direction may displace the drive coupling in the distal direction and may rotate the drive coupling. Rotating the drive coupling may lock the drive coupling to the syringe coupling, as explained in greater detail below. In some embodiments, the reusable portion may include a plunger configured to transmit axial motion of the motor foot to a moveable seal of the disposable portion.

In some embodiments, a method of operating an autoinjector may include translating a motor foot coupled to an output of a motor in a distal direction to cause the motor foot to contact a drive coupling. The drive coupling may in turn translate in the distal direction to contact a syringe coupling. Rotating the drive coupling relative to the syringe coupling may lock the drive coupling to the syringe coupling. Translating the drive coupling and syringe coupling together in the distal direction may deploy a needle of a syringe associated with the syringe coupling. Afterwards, translating the motor foot relative to the drive coupling in the distal direction may cause the motor foot to contact a plunger disposed at least partially within a cavity of the syringe. Continuing to translate the motor foot in the distal direction may displace the plunger, which may in turn displace a moveable seal disposed within the cavity of the syringe, thereby delivering a material disposed within the syringe through the needle.

In some embodiments, operating an autoinjector may include the steps of needle insertion, drug delivery, and needle retraction. These steps may be performed automatically by the autoinjector after a user engages a device actuator. In some embodiments, a single motor may perform all of the steps of needle insertion, drug delivery, and needle retraction.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

By way of illustration, the medication delivery device is described in the form of an autoinjector. However, the medication delivery device may be any device which is used to set and to deliver a dose of a medication, such as pen injectors, infusion pumps and syringes. The medication may be any of a type that may be delivered by such a medication delivery device. The device may be configured for a single fixed dose injection or a series of fixed dosage injections. Other embodiments of devices could be configured for a series of variable doses. The device may include a disposable device after the exhaustion of the medication or a reusable device capable of receiving a new cartridge of medication after exhaustion of the used cartridge of medication.

FIG. 1 is a perspective view of one embodiment of an autoinjector 100. The autoinjector 100 includes a housing 102 with a proximal portion 104 and a distal portion 106, each disposed along a longitudinal axis LA (shown in FIG. 2). The terms "proximal" and "distal" used herein are from a reference from the user actuator, with the proximal direction being toward the direction of the user actuator and the distal direction being in the opposite direction, that is toward the treatment site. The housing 102 may define an internal cavity 105 in which the components described herein may fit within. The proximal portion 104 of the housing 102 may include a device actuator 120 configured to initiate an injection of the autoinjector 100. The device actuator 120 may comprise a button, a switch, or any other suitable component configured to initiate an autoinjector. A base cap 110 may be removably coupled to the distal portion 106 of the housing 102. The base cap 110 may be configured to cover the distal portion 106 of the housing 102. In some embodiments, the base cap 110 may include a syringe removal tool 112, described in greater detail below.

Figure 2:
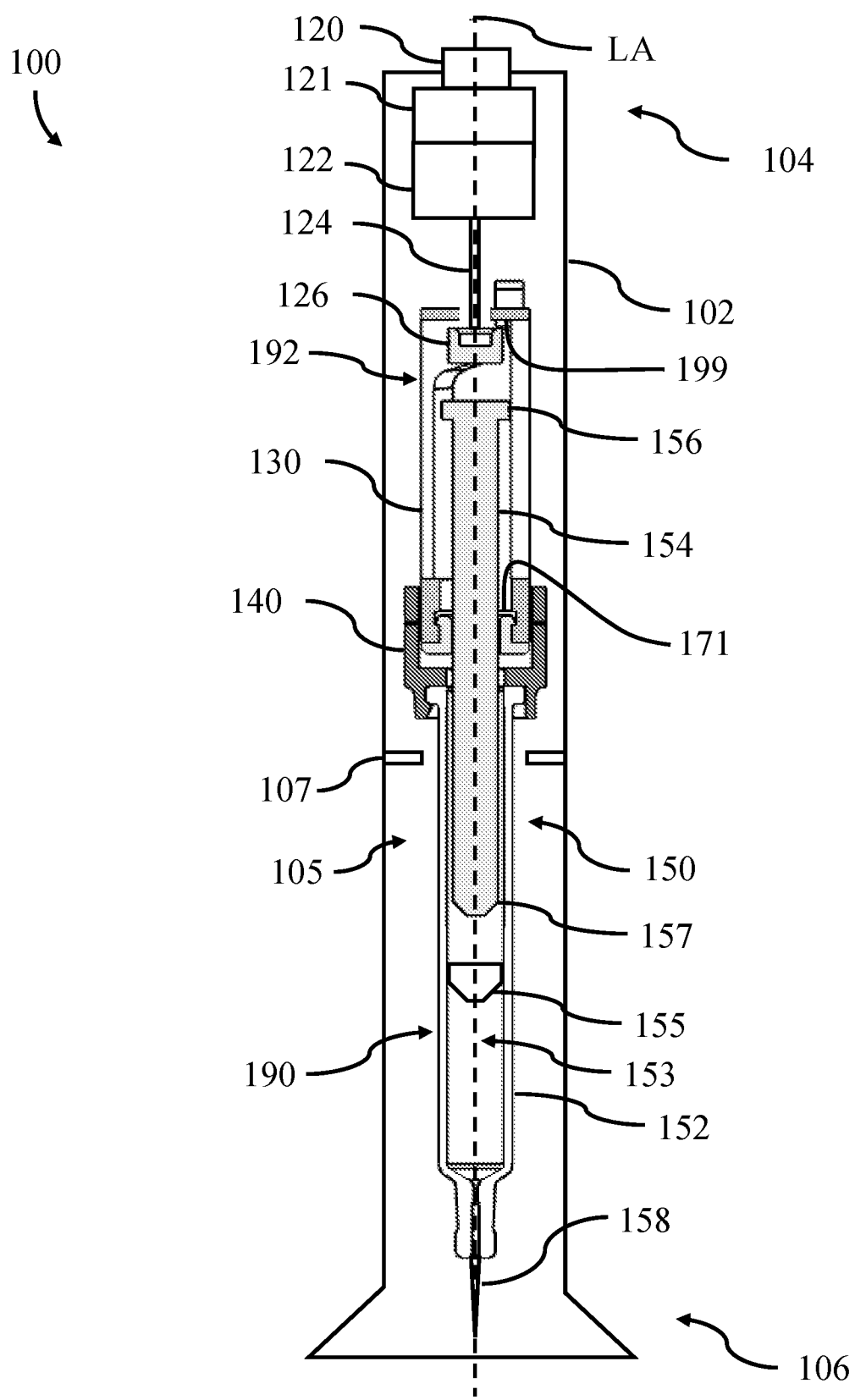
FIG. 2 is a front cross-sectional view of the autoinjector of FIG. 1.

FIG. 2 is a front cross-sectional view of the autoinjector 100 of FIG. 1. At the proximal portion 104 of the autoinjector 100, the device actuator 120 is coupled to a motor 122, such that actuating the device actuator 120 activates the motor 122. In some embodiments, the autoinjector 100 may include a controller configured to control operation of the autoinjector 100. For example, a controller 121 may be coupled to the device actuator 120 and the motor 122. The controller 121 may read signals sent by the device actuator 120, such that when a user actuates the device actuator 120, the controller 121 may initiate an injection procedure that may include providing power to the motor 122.

An output of the motor 122 may be coupled to a motor foot 126 through a transmission 124. In some embodiments, the transmission 124 may convert a rotational motion of the motor 122 into a linear motion. In others, the transmission and motor may form a linear actuator with a reciprocating shaft coupled to the foot for translating the foot. The motor 122 may be configured to cause the motor foot 126 to translate in an axial direction. As the motor foot 126 translates in a distal direction (i.e., toward the distal portion 106 of the housing 102), the motor foot 126 may engage with an angled surface 134 of a drive coupling 130 (see FIGS. 3a-3b). Continued distal translation of the motor foot 126 may axially translate the drive coupling 130 until the motor foot 126 contacts a syringe coupling 140, causing the syringe coupling 140 to translate. Translation of the syringe coupling 140 may cause a needle 158 of a syringe 150 coupled to the syringe coupling 140 to define a syringe assembly 190 to be deployed. Deploying the needle 158 may include at least a portion of the needle extending distally out of the autoinjector housing 102 and inserting into a user operating the autoinjector 100. Drive assembly 192 may be a combination of one or more of the device actuator 120, the controller 121, motor 122, motor foot 126, transmission 124, plunger 154, and other components associated with these features.

After needle insertion, further translation of the motor foot 126 may cause rotation of the drive coupling 130, which may lock the drive coupling 130 to the syringe coupling 140. After the drive coupling 130 is locked to the syringe coupling 140, the motor foot 126 may disengage with the angled surface of the drive coupling 130 and may continue to translate in the distal direction until the motor foot 126 contacts a proximal portion 156 of a plunger. In some embodiments, a distal portion 157 of the plunger 154 may be disposed within a cavity 153 of a body 152 of the syringe 150. FIG. 2 shows the motor foot 126 can be initially in an axially spaced relationship with the proximal portion 156. As the motor foot 126 continues to translate, the plunger 154 may be displaced relative to the syringe body 152. In some embodiments, the distal portion 157 of the plunger 154 is configured to contact a moveable seal 155 that is also disposed within the cavity 153 of the syringe body 152. In some embodiments, the moveable seal 155 may be spaced from the plunger 154 prior to device actuation.

In the illustrative embodiment shown in FIG. 2, the plunger 154 and the moveable seal 155 are two separate and distinct components. The plunger may, in some embodiments, be part of a reusable portion of an autoinjector, while the moveable seal may, in some embodiments, be part of a disposable portion of an autoinjector.

It should be appreciated, however, that in some alternative embodiments, the moveable seal 155 may be integrated with the plunger 154 as a single component.

Regardless, displacing the moveable seal 155 in a distal direction may dispense a material, such as a medication, disposed within the syringe 150 through the needle 158. Dispensing a material disposed within the syringe 150 may include injecting a medication into the user of the autoinjector 100.

Devices described herein, such as autoinjector 100, or other kinds of injector devices that may incorporate the elements of this disclosure, may further comprise medication, such as for example, within a reservoir provided by the syringe. In another embodiment, a system may comprise one or more devices including device and a medication. The term "medication" refers to one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, oxyntomodulin analogs, oxyntomodulin derivatives, therapeutic antibodies and any therapeutic agent that is capable of delivery by the above device. The medication as used in the device may be formulated with one or more excipients. The device is operated in a manner generally as described above by a patient, caregiver or healthcare professional to deliver medication to a person.

After injection, the direction of the motor 122 may be reversed to retract the needle 158. Motor reversal and needle retraction may be performed automatically, and may not require any additional input from the user. For example, the controller 121 may begin needle retraction after a certain amount of time has elapsed since the beginning of the procedure, or may wait to receive signals from one or more sensors configured to measure an amount of material in the syringe 150. Reversing the direction of the motor 122, or retracting the shaft, may cause the motor foot 126 to translate in a proximal direction. After sufficient translation, the motor foot 126 may contact an interior proximal portion 138 (see FIGS. 4A and 4B) of the drive coupling 130, such that additional translation of the motor foot 126 in the proximal direction may translate the locked drive coupling 130 and syringe coupling 140 together in the proximal direction. Translating the syringe coupling 140 in the proximal direction may translate the syringe 150 and the needle 158 in the proximal direction, thereby retracting the needle 158 back into the autoinjector housing 102.

Figure 3A:
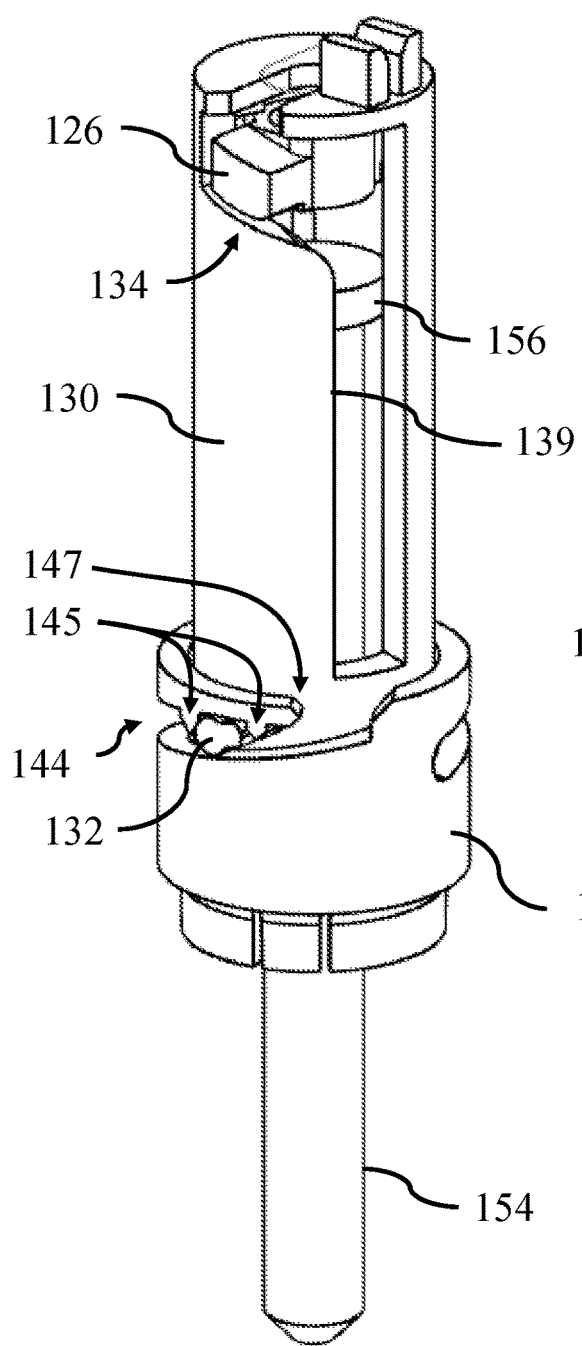
FIG. 3A is a perspective view of one embodiment of a drive system of an autoinjector.
Figure 3B:
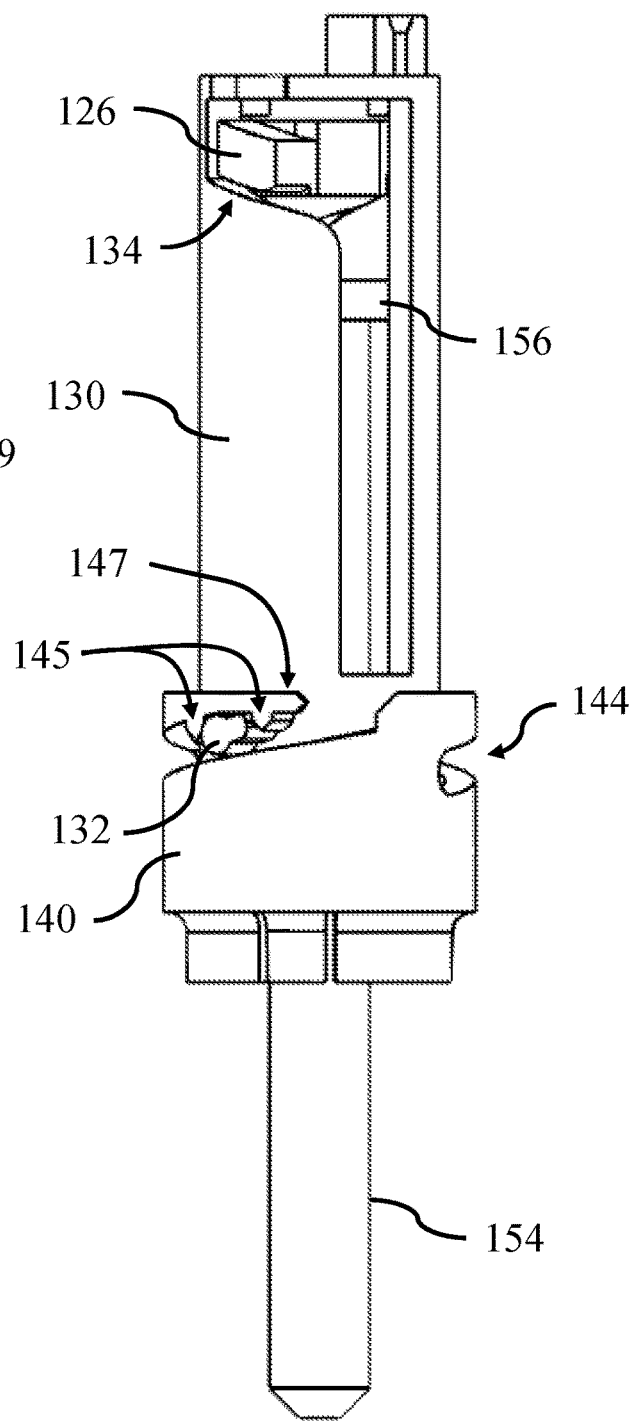
FIG. 3B is a front view of the drive system of FIG. 3A.

FIGS. 3A and 3B depict one embodiment of at least a portion of a drive system of an autoinjector. In some embodiments, a drive system may include a motor (see motor 122 in FIG. 2), a motor foot 126, a drive coupling 130, a syringe coupling 140, and a plunger 154. In some embodiments, additional components may be included in a drive system of an autoinjector, while in some embodiments, one or more of the above-noted components may be absent from a drive system of an autoinjector, as the disclosure is not limited in this regard. As shown in the figure, the drive coupling 130 may include an angled surface 134 configured to receive the motor foot 126. The angled surface 134 may act as a cam surface that translates linear motion of the motor foot 126 into rotational motion of the drive coupling 130. The drive coupling 130 may include a radial protrusion 132 configured to engage with a guide track 144 of the syringe coupling 140 to lock the drive coupling 130 to the syringe coupling 140. In some embodiments, the guide track 144 of the syringe coupling 140 may be sloped. In some embodiments, an angle of the angled surface 134 may determine, at least in part, an amount of rotation of the drive coupling 130 when the motor foot 126 contacts the angled surface 134. The angle of the angled surface 134 may also determine the amount of distal translation (indicated in a distal direction by arrow 181 in FIG. 6D) and rate of the drive coupling and the syringe coupling together as a unit to deploy the needle beyond the device housing.

Figure 5A:
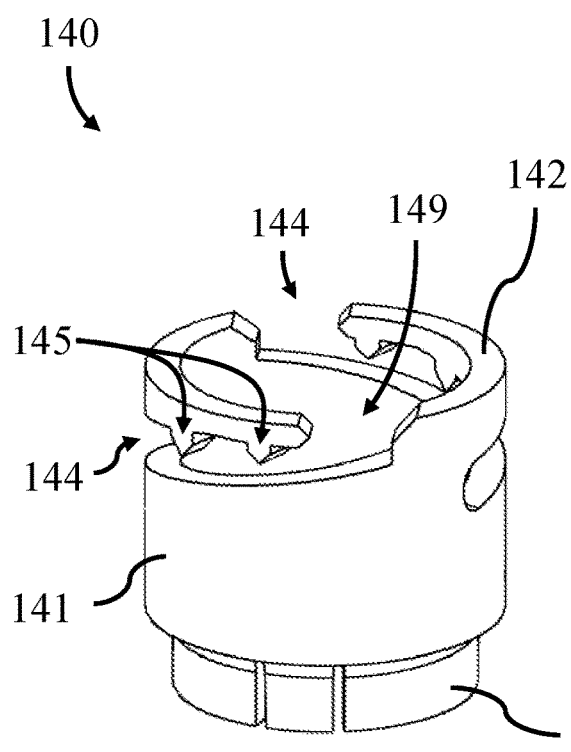
FIG. 5A is a perspective view of one embodiment of a syringe coupling of an autoinjector.
Figure 5B:
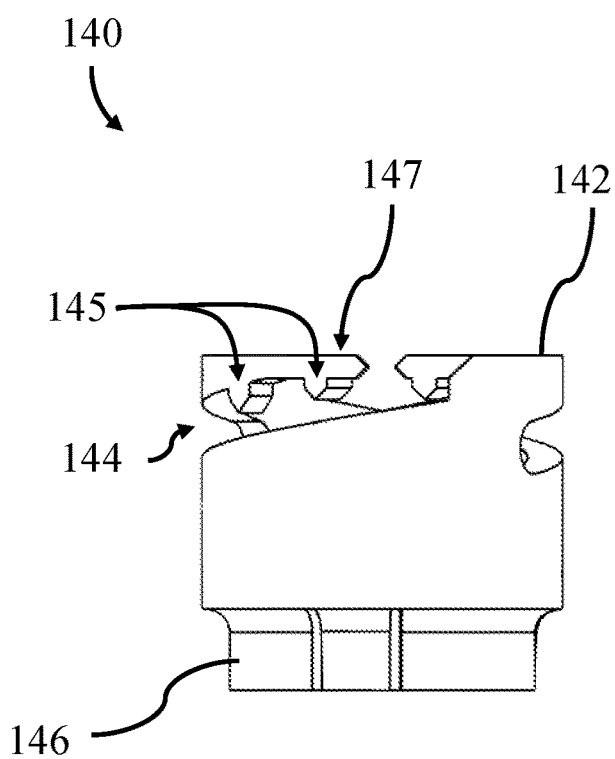
FIG. 5B is a front view of the syringe coupling of FIG. 5A.

In FIGS. 5A-5B, guide track 144 may be a slot defined by the outer wall 141 of the syringe coupling 140 and track 144 may form part of a helical pattern. One or more track protrusions 145 may be extending distally within the spacing of track 144. Two track protrusions are shown, and the radial protrusion 132 is shown being moved from right of first of track protrusions 145 (right most in figure), in between track protrusions 145, to left of second of track protrusions 145 (left most in figure). When radial protrusion 132 is disposed between track protrusions 145, this provides initial axial and rotational locking of the syringe assembly 190 to the drive assembly. During coupling, the radial protrusion 132 enters the opening of the track 144, continues passed the first protrusion 145 and is kept in between the protrusions 145 by the second protrusion 145, as shown in FIG. 6C). During coupling and decoupling, the tip portion 147 of the syringe coupling 140 adjacent the opening 149 of the guide track 144 may flex proximally as the radial protrusion 132 slidably engages the tip portion 147 and the first protrusion 145. As the syringe coupling 140 is rotationally fixed and the drive coupling rotates relative to the syringe coupling, the radial protrusion 132 will move in the first rotational direction (arrow 183 in FIGS. 6C and 6D) to clear the second of track protrusions 145 and continue to be move within the guide track 144 until reaching the circumferential end surface of the guide track 144 which physically stops additional relative rotation. To decouple the syringe coupling 140 as described below, the user rotates the syringe coupling 140 relative to the drive coupling 130 in direction opposite the first rotational direction 153 such that the radial protrusion 132 travels within the guide track 144 and beyond (right of) the first of track protrusions 145 to opening 149 of the guide track 144.

After a predetermined amount of rotation of the drive coupling 130 relative to the syringe coupling 140, the motor foot 126 may disengage with (e.g., slide out of contact with) the angled surface 134 of the drive coupling 130. As the motor foot continues to translate in a distal direction, the motor foot may contact a proximal portion 156 of the plunger 154. The motor foot 126 may be configured to displace the plunger 154. In some embodiments, the plunger 154 may extend through the syringe coupling 140 such that a proximal portion of the plunger 154 is proximal to a proximal portion of the syringe coupling 140.

Figure 4A:
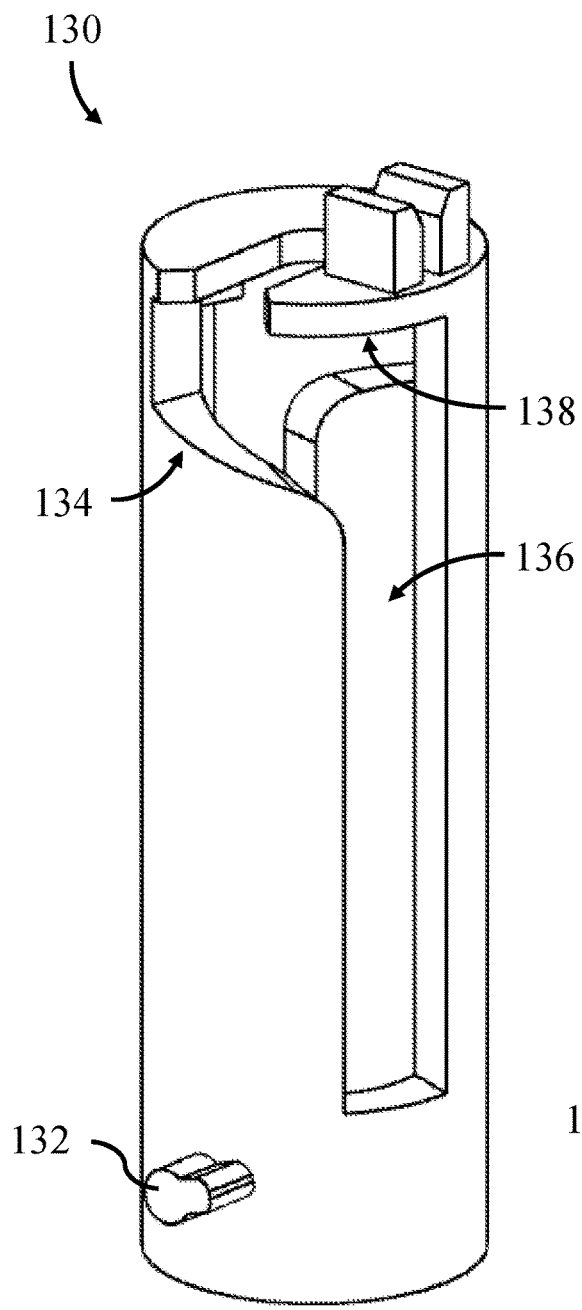
FIG. 4A is a perspective view of one embodiment of a drive coupling of an autoinjector.
Figure 4B:
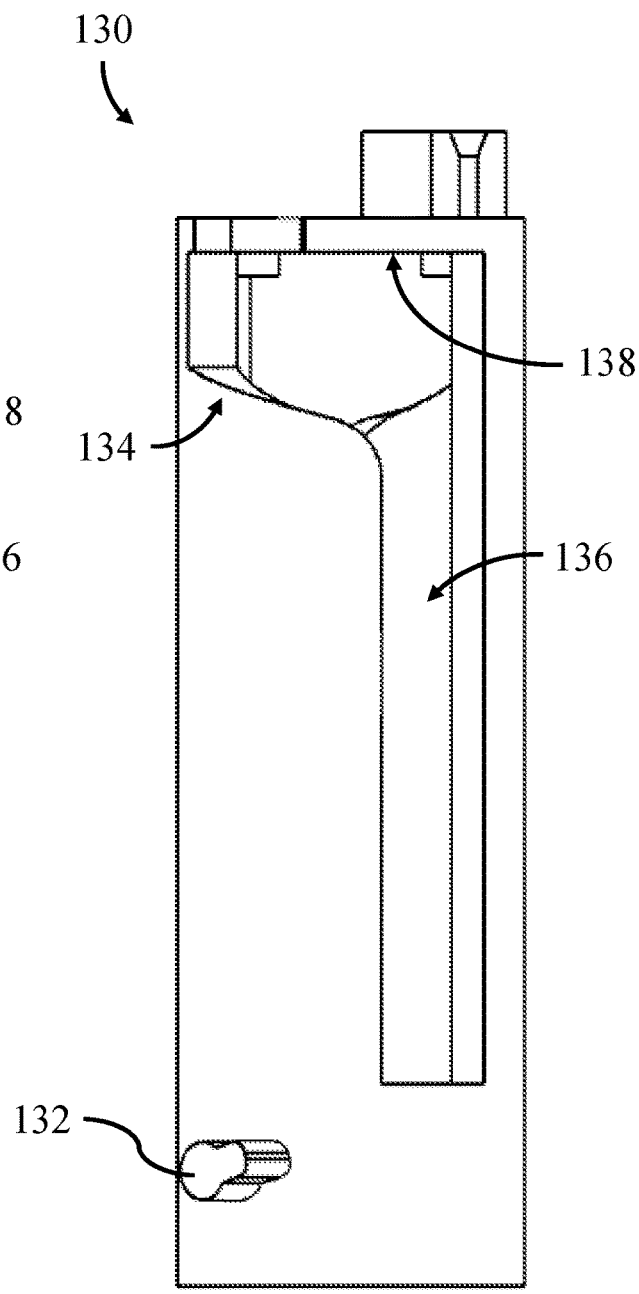
FIG. 4B is a front view of the drive coupling of FIG. 4A.

FIGS. 4A and 4B depict one embodiment of a drive coupling 130 of an autoinjector in greater detail. As previously discussed, the drive coupling 130 may include an angled surface 134 configured to receive a motor foot, as well as a protrusion 132 configured to engage with a guide track of a syringe coupling to lock the drive coupling 130 to the syringe coupling. In some embodiments, the drive coupling 130 may include a plurality of protrusions 132 disposed around a circumference of the drive coupling. For example, the drive coupling 130 may include two protrusions 132 disposed at 180 degrees relative to each other. It should be appreciated that any suitable number of protrusions disposed at any suitable position relative to one another may be used. The drive coupling 130 may additionally define axial wall surfaces 139 for defining an axial slot 136, wall surface 139 being contiguous with the angled surface 134, in which the motor foot may translate as the motor foot depresses a plunger. An interior proximal surface 138 of the drive coupling may be configured to receive the motor foot as the motor foot translates in a proximal direction during needle retraction. In some embodiments, a drive coupling 130 may include a plurality of slots 136, as the disclosure is not limited in this regard. The angled surface 134 and one of the axial slot walls may define a continuous contiguous wall surface for guiding the foot.

FIGS. 5A and 5B depict one embodiment of a syringe coupling 140 of an autoinjector in greater detail. As previously discussed, the syringe coupling 140 may include a guide track 144 configured to receive a protrusion of a drive coupling to lock the syringe coupling 140 to the drive coupling from a first rotational relative movement between the syringe coupling 140 and the drive coupling 130. The syringe coupling 140 and the drive coupling 130 may be decoupled from one another by a second rotational relative movement in the opposite direction. In some embodiments, a syringe coupling 140 may include a plurality of guide tracks 144. For example, a syringe coupling 140 may include two guide tracks 144 disposed at 180 degrees relative to each other. The syringe coupling 140 may additionally include a contact rim 142 configured to contact the drive coupling, and a flange 146 configured to couple to a body of a syringe. The flange and the body of the syringe may be coupled via a press fit, adhesive, welding, mechanical interlock, or any other suitable arrangement. In some embodiments, the flange 146 ensures that the syringe coupling 140 is rotationally fixed relative to the body of the syringe.

FIGS. 6A-6F depict a sequence of steps in one embodiment of a method of operating an autoinjector. In FIG. 6A, syringe coupling 140 of the syringe assembly (which is hidden in FIGS. 6A-6F) with is inserted axially (shown by arrow 194) within the device housing, preferably at a predefined relative angular orientation by which protrusion 132 of the drive coupling 130 is in alignment with the opening 149 of the guide track 144 of the syringe coupling 140. In FIG. 6B the protrusion 132 is shown axially spaced from the proximally facing surface 144A of the guide track 144, although the protrusion may be placed in engagement with surface 144A. Also, in FIG. 6B, a motor foot 126 translates in a distal direction 181. In some embodiments, the motor foot 126 may be coupled to an output of a motor. In some embodiments, a device actuator may be operated to actuate the motor and/or to initiate translation of the motor foot. In some embodiments, operating a device actuator may include depressing a button. The motor foot 126 contacts an angled surface 134 of a drive coupling 130. In FIG. 6C, the motor foot 126 and the drive coupling 130 translate together relative to the stationary syringe coupling as the motor foot 126 exerts an axial force on the angled surface 134. For example, after the drive coupling 130 translates a predetermined distance in the distal direction, the drive coupling 130 contacts a syringe coupling 140, and a protrusion 132 of the drive coupling 130 engages and traverses with a guide track 144 of the syringe coupling 140. Once protrusion is in predefined location within track 144, the motor foot 126, drive coupling 130, and syringe coupling 140 translate together in the distal direction 181 to deploy a needle of a syringe (not shown) associated with the syringe coupling 140. An interior shoulder 107 extending in housing cavity 105 radially from the device housing 102 may be formed along the axial portion of the device housing, which is shown in FIG. 2. The shoulder 107 provides a stop surface that the syringe coupling/drive coupling as unit will engage to determine total extent of travel of the syringe assembly for deploying needle.

In one embodiment, the autoinjector may be configured to automatically couple the drive coupling 130 to syringe coupling 140 of syringe assembly 190 once inserted axially, such as described above. The coupling together manually performed by the user. For example, the user axially moves the syringe assembly within the housing such that the protrusion 132 in in engagement with surface 144A. The user applies a rotational force to the syringe assembly in the first rotational direction 183 relative to the drive coupling 130 sufficient to clear the first of track protrusions 145 (which its initial coupling position is shown in FIG. 6D).

When translation of the drive coupling 130 in the distal direction 181 encounters sufficient resistance, the motor foot 126 engaging with the angled surface 134 of the drive coupling 130 causes the drive coupling 130 to rotate relative to the syringe coupling 140 that remains rotationally fixed relative to the device housing, as seen in FIG. 6D. As the drive coupling 130 rotates in the first rotational direction 183, the protrusion 132 is displaced along the guide track 144 of the syringe coupling 140, thereby further locking the drive coupling 130 to the syringe coupling 140 in a pre-defined relative angular orientation between them. In FIG. 6E, after a predetermined amount of rotation of the drive coupling 130, the motor foot 126 disengages with the angled surface 134 of the drive coupling 130 and enters a slot 136 of the drive coupling 130. As the motor foot 126 translates in the distal direction in the slot 136, the motor foot contacts a proximal portion 156 of a plunger 154. In one embodiment, the motor foot is axially displaced away from the plunger proximal portion 156 by a gap (shown in FIG. 3A) prior to entering into slot 136 where the motor foot closes the gap to engage the plunger end. In FIG. 6F, further translation of the motor foot 126 displaces the plunger 154, which in turn displaces a moveable seal 155 (see FIG. 2), thereby delivering a material disposed within the syringe through the needle.

The proximal portion 156 of the plunger 154 engages a stop 171 formed by an interior flange of the drive coupling 130 (as shown in FIG. 2) when the plunger 154 has reached a full injection stroke length to deliver the material. After injection, the motor foot 126 is movable proximally to disengage from the proximal portion 156 of the plunger 154 until the motor foot 126 engages with the interior proximal portion 199 of the drive coupling (also shown in FIG. 2). When this engagement, the motor foot 126 continues to move proximally and the drive coupling and the syringe coupling together as a unit are moved for an amount of proximal translation to retract the needle 158 inside the device housing. After retraction, the syringe assembly 190 can be rotated, manually by user or automatically by device, and then distally translated relative to the drive coupling that remains rotationally locked relative to the device housing. During this action, the radial protrusion 132 of the drive coupling is cleared from the guide track 144 of the syringe coupling 140 for allowing the syringe assembly 190 to be entirely removed from the housing with the drive assembly. After which, a new syringe assembly can be inserted within the housing in the manner described herein.

Figures 7A, 7B:
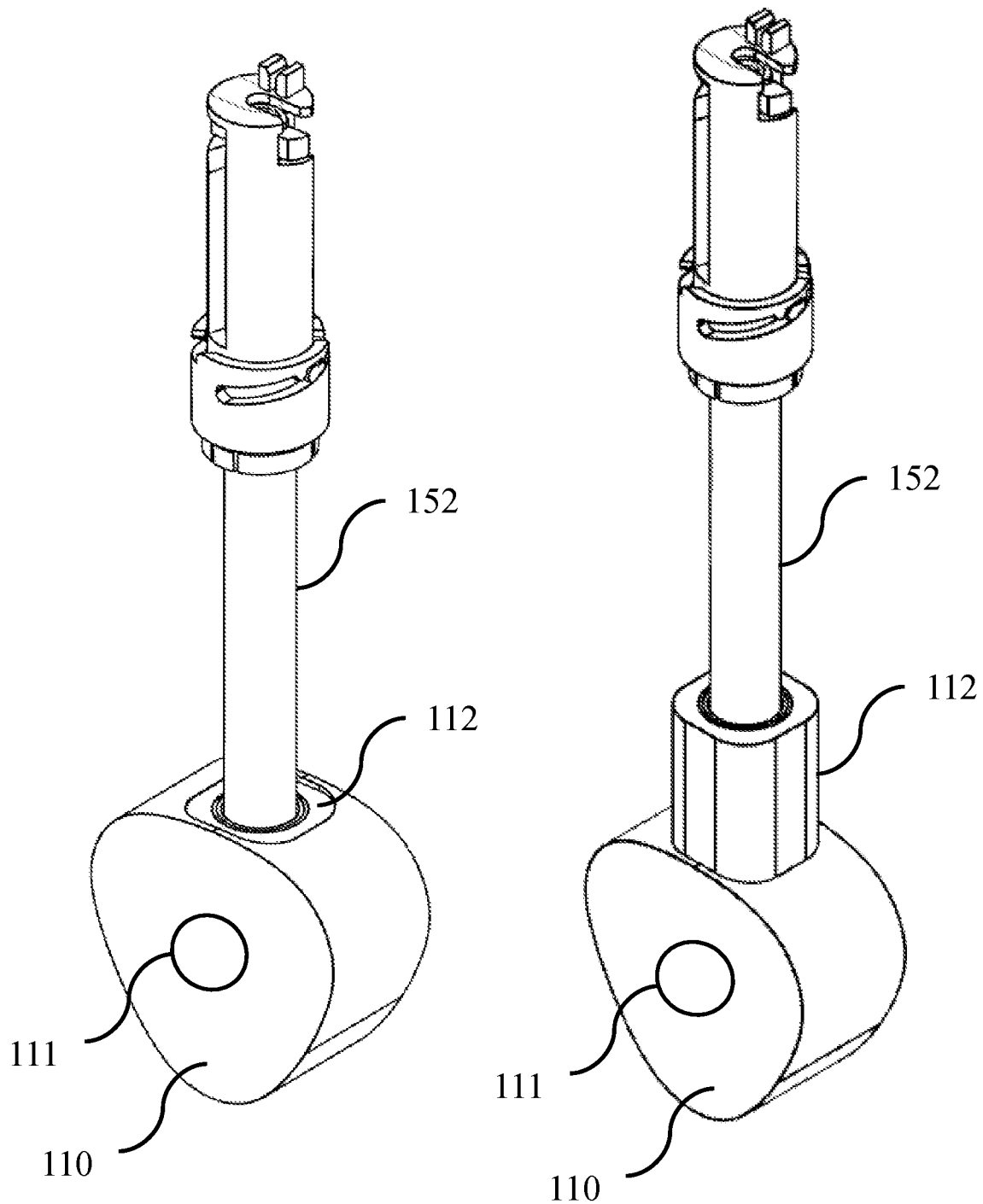
FIG. 7A depicts one embodiment of a syringe removal tool in a retracted configuration.
FIG. 7B depicts the syringe removal tool of FIG. 7A in an extended configuration.

FIGS. 7A and 7B depict one embodiment of a syringe removal tool 112 in retracted and extended configurations, respectively. As described above, the syringe removal tool 112 may be integrated into a base cap 110 of an autoinjector. The base cap 110 may include a first opening 111 configured to receive a distal portion of an autoinjector housing 102 when the autoinjector 100 is not in use, such as in FIG. 1. In some embodiments, the first opening 111 may be configured to receive a needle of an autoinjector. A user may remove the base cap 110 from the autoinjector housing 102 prior to initiating an injection. After the injection, the user may retrieve the base cap 110 to remove the disposable portion of the autoinjector from the reusable portion. In some embodiments, the syringe removal tool may have a retracted configuration (FIG. 7A) and an extended configuration (FIG. 7B). In some embodiments, the syringe removal tool 112 may be slidably coupled to the base cap 110 such that the syringe removal tool 112 may translate between the retracted configuration and the extended configuration.

Figure 7C:
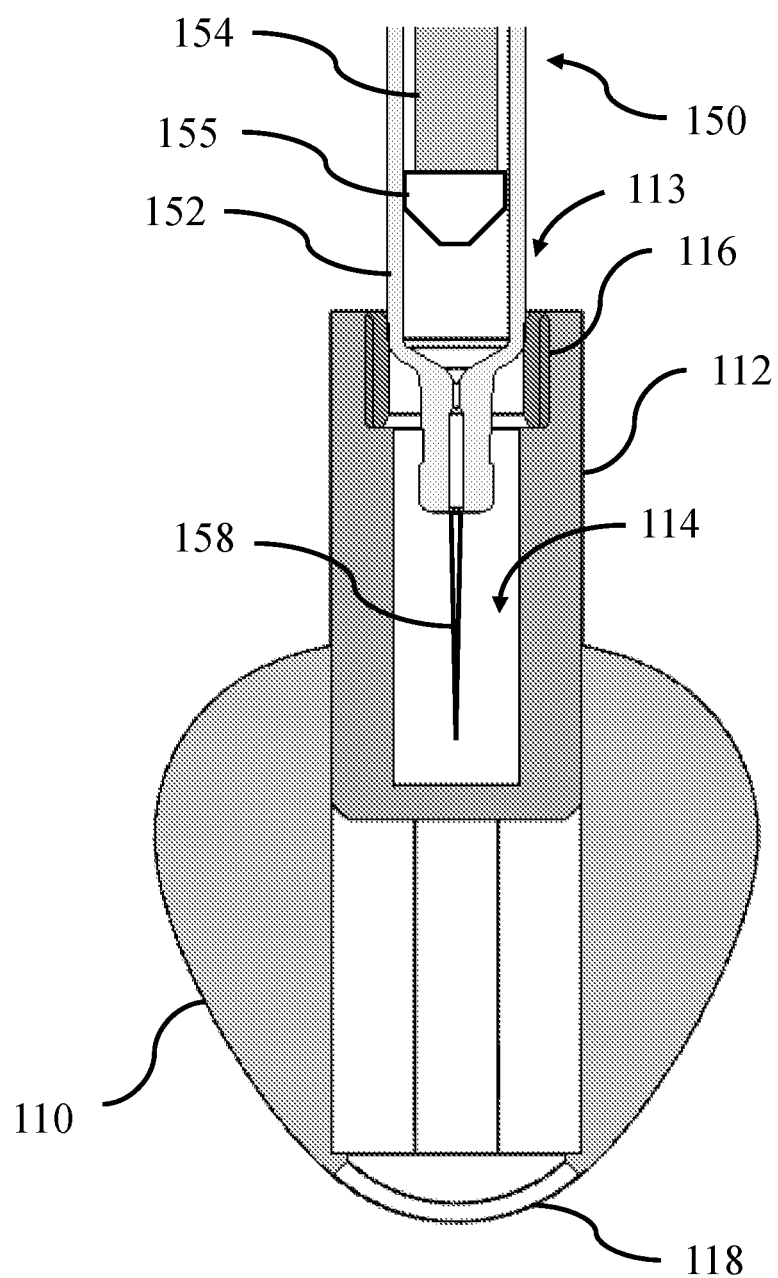
FIG. 7C is a cross-sectional view of one embodiment of a syringe removal tool removing a syringe from an autoinjector.

FIG. 7C is a cross-sectional view of one embodiment of a syringe removal tool removing a syringe from an autoinjector. The base cap 110 may include a button 118 that, when pressed by a user, moves the syringe removal tool 112 into the extended configuration. The syringe removal tool 112 includes a second opening 113 that allows access to a cavity 114. After injection of a medication, a user may engage the distal portion of the autoinjector with the syringe removal tool 112 such that a needle 158 of the syringe 150 is inserted through the second opening 113 and into the cavity 114. During insertion of the needle 158 into the cavity 114, contact surfaces 116 of the syringe removal tool 112 may radially engage with a body 152 of the syringe 150, thereby preventing any further relative movement of the syringe body 152 relative to the syringe removal tool 112. In some embodiments, the second opening 113 may be sized to provide a frictional fit when engaged with the syringe body 152. In some embodiments, the contact surfaces 116 may be made of an elastomer material. After the contact surfaces 116 engage with the syringe body 152, the user may rotate the autoinjector housing relative to the base cap 110 (and, therefore, relative to the syringe removal tool 112). The rotation of the autoinjector housing may uncouple the syringe coupling from the drive coupling. In some embodiments, rotation the autoinjector may cause the radial protrusion of the drive coupling to translate back along the guide track to the guide track opening, clearing the first track protrusion, of the syringe coupling until the protrusion is removed from the guide track, thereby unlocking the syringe coupling from the drive coupling. As the user separates the base cap 110 from the autoinjector housing, the needle, the syringe, and syringe coupling may be retained in the base cap 110 and removed from the autoinjector housing. In this way, the disposable portion of the autoinjector may be separated from the reusable portion of the autoinjector.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

Aspects

1. An assembly of an autoinjector, the assembly including: a syringe including: a body having a proximal portion and a distal portion, the body including an internal cavity; a moveable seal at least partially disposed within the internal cavity of the body; and a needle coupled to the distal portion of the body; and a syringe coupling coupled to the body of the syringe, the syringe coupling including a guide track configured to receive a radial protrusion of a drive coupling to lock the syringe coupling to the drive coupling.

2. The assembly of aspect 1, further including a syringe removal tool configured to unlock the syringe coupling from the drive coupling and remove the syringe coupling from the drive coupling.

3. The assembly of aspect 2, further including a base cap configured to couple to a distal portion of a device housing of the autoinjector, wherein the syringe removal tool is integrated into the base cap, the syringe removal tool having an opening configured to receive the needle.

4. The assembly of any one of aspects 1-3, wherein the syringe coupling is rotationally fixed relative to the body of the syringe.

5. The assembly of any one of aspects 1-4, wherein the guide track of the syringe coupling is sloped.

6. An autoinjector, including: a first assembly including the assembly of any one of aspects 1-5; and a second assembly including: a device housing having a proximal portion and a distal portion; a device actuator configured to initiate an injection of the autoinjector; a motor coupled to the device actuator, the motor having an output; a motor foot coupled to the output of the motor, the motor foot configured to translate in an axial direction; and a drive coupling disposed within the device housing, the drive coupling including: an angled surface configured to receive the motor foot; and a radial protrusion configured to engage with a guide track of a syringe coupling to lock the drive coupling to the syringe coupling.

7. The autoinjector of aspect 6, further including a plunger at least partially disposed within the internal cavity of the body of the syringe, wherein the plunger extends through the syringe coupling such that a proximal portion of the plunger is proximal to a proximal portion of the syringe coupling.

8. An assembly of an autoinjector, the assembly including: a device housing having a proximal portion and a distal portion; a device actuator configured to initiate an injection of the autoinjector; a motor coupled to the device actuator, the motor having an output; a motor foot coupled to the output of the motor, the motor foot configured to translate in an axial direction; and a drive coupling disposed within the device housing, the drive coupling including: an angled surface configured to receive the motor foot; and a protrusion configured to engage with a guide track of a syringe coupling to lock the drive coupling to the syringe coupling.

9. The assembly of aspect 8, further including a syringe assembly including a syringe body having a proximal portion and a distal portion and defining a cavity, a moveable seal at least partially disposed within the cavity of the syringe body, and a needle coupled to the distal portion of the body, and a syringe coupling coupled to the syringe body, the syringe coupling including a guide track configured to receive said protrusion of said drive coupling to lock the syringe coupling to the drive coupling.

10. The assembly of aspect 9, wherein an angle of the angled surface determines, at least in part, an amount of rotation of the drive coupling when the motor foot contacts the angled surface of the drive coupling, and an amount of distal translation of the drive coupling and the syringe coupling together as a unit to deploy the needle beyond the device housing.

11. The assembly of aspect 10, wherein the drive coupling includes a plunger having a distal portion insertable within the cavity to contact the moveable seal, wherein the drive coupling defines an axial slot having a wall surface contiguous with the angled surface, wherein when the motor foot clears the angled surface the motor foot is entered into the axial slot and is moved distally for engagement with a proximal portion of the plunger to drive the plunger toward the needle.

12. The assembly of aspect 11, wherein the proximal portion of the plunger engages a stop formed by the drive coupling when the plunger has reached an injection stroke length, wherein the motor foot is movable proximally and in disengagement from the proximal portion of the plunger until the motor foot engages with an interior proximal portion of the drive coupling at which the drive coupling and the syringe coupling together as a unit are moved for an amount of proximal translation to retract the needle inside the device housing.

13. The assembly of any one of aspects 9-12, wherein the syringe coupling includes a pair of protrusions extending distally within the guide track and configured to receive said protrusion of said drive coupling to lock the syringe coupling to the drive coupling, and, in response to rotation and distal translation of said syringe assembly relative to the drive coupling, said protrusion of said drive coupling is cleared from the guide track of said syringe coupling to allow the syringe assembly to be removed from said assembly.

14. A method of operating an autoinjector, the method including: coupling a syringe coupling of a syringe assembly to a drive coupling of the autoinjector; translating a motor foot coupled to an output of a motor in a distal direction to cause the motor foot to contact said drive coupling; rotating the drive coupling relative to the syringe coupling; translating the drive coupling and syringe coupling together in the distal direction, thereby deploying a needle of the syringe assembly associated with the syringe coupling; and translating the motor foot relative to the drive coupling in the distal direction to cause the motor foot to displace a moveable seal of the syringe assembly, thereby delivering a material disposed within the syringe assembly through the needle.

15. The method of aspect 14, further including translating the motor foot in a proximal direction to cause the motor foot to contact the drive coupling, thereby translating the locked drive coupling and syringe coupling together in the proximal direction, thereby retracting the needle.

16. The method of any one of aspects 14-15, further including: coupling a syringe removal tool to the syringe; rotating the syringe removal tool relative to an autoinjector housing, thereby unlocking the drive coupling from the syringe coupling; and moving the autoinjector housing away from the syringe removal tool, thereby removing the needle, the syringe, and the syringe coupling from the autoinjector housing.

17. The method of any one of aspects 14-16, further including operating a device actuator to initiate translation of the motor foot.

18. The method of aspect 17, wherein operating the device actuator includes depressing a button.

19. The method of any one of aspects 14-16, wherein rotating the drive coupling relative to the syringe coupling includes contacting an angled surface of the drive coupling with the motor foot.

20. The method of any one of aspects 14-16, wherein coupling the syringe coupling of the syringe assembly to the drive coupling of the autoinjector includes displacing a protrusion of the drive coupling in a guide track of the syringe coupling.

What is claimed is:

1. An autoinjector, comprising: a first assembly comprising a syringe and a syringe coupling, the syringe comprising a body having a proximal portion and a distal portion, the body comprising an internal cavity, a moveable seal at least partially disposed within the internal cavity of the body, and a needle coupled to the distal portion of the body, the syringe coupling coupled to the body of the syringe, the syringe coupling comprising a guide track configured to receive a radial protrusion of a drive coupling to lock the syringe coupling to the drive coupling; a second assembly comprising: a device housing having a proximal portion and a distal portion; a device actuator configured to initiate an injection of the autoinjector; a motor coupled to the device actuator, the motor having an output; a motor foot coupled to the output of the motor, the motor foot configured to translate in an axial direction; and a drive coupling disposed within the device housing, the drive coupling comprising: an angled surface configured to receive the motor foot; and the radial protrusion configured to engage with the guide track of the syringe coupling to lock the drive coupling to the syringe coupling.

2. The autoinjector of claim 1, further comprising a syringe removal tool configured to unlock the syringe coupling from the drive coupling and remove the syringe coupling from the drive coupling.

3. The autoinjector of claim 2, further comprising a base cap configured to couple to a distal portion of a device housing of the autoinjector, wherein the syringe removal tool is integrated into the base cap, the syringe removal tool having an opening configured to receive the needle.

4. The autoinjector of claim 1, wherein the syringe coupling is rotationally fixed relative to the body of the syringe.

5. The autoinjector of claim 1, wherein the guide track of the syringe coupling is sloped.

6. The autoinjector of claim 1, further comprising a plunger at least partially disposed within the internal cavity of the body of the syringe, wherein the plunger extends through the syringe coupling such that a proximal portion of the plunger is proximal to a proximal portion of the syringe coupling.

7. The autoinjector of claim 1, further comprising a medication disposed within the internal cavity of the body of the syringe.

8. An assembly of an autoinjector, the assembly comprising:
   a device housing having a proximal portion and a distal portion;
   a device actuator configured to initiate an injection of the autoinjector;
   a motor coupled to the device actuator, the motor having an output;
   a motor foot coupled to the output of the motor, the motor foot configured to translate in an axial direction; and
   a drive coupling disposed within the device housing, the drive coupling comprising:
      an angled surface configured to receive the motor foot; and
      a protrusion configured to engage with a guide track of a syringe coupling to lock the drive coupling to the syringe coupling.

9. The assembly of claim 8, further comprising a syringe assembly comprising a syringe body having a proximal portion and a distal portion and defining a cavity, a moveable seal at least partially disposed within the cavity of the syringe body, and a needle coupled to the distal portion of the body, and a syringe coupling coupled to the syringe body, the syringe coupling comprising a guide track configured to receive said protrusion of said drive coupling to lock the syringe coupling to the drive coupling.

10. The assembly of claim 9, wherein an angle of the angled surface determines, at least in part, an amount of rotation of the drive coupling when the motor foot contacts the angled surface of the drive coupling, and an amount of distal translation of the drive coupling and the syringe coupling together as a unit to deploy the needle beyond the device housing.

11. The assembly of claim 10, wherein the drive coupling comprises a plunger having a distal portion insertable within the cavity to contact the moveable seal, wherein the drive coupling defines an axial slot having a wall surface contiguous with the angled surface, wherein when the motor foot clears the angled surface the motor foot is entered into the axial slot and is moved distally for engagement with a proximal portion of the plunger to drive the plunger toward the needle.

12. The assembly of claim 11, wherein the proximal portion of the plunger engages a stop formed by the drive coupling when the plunger has reached an injection stroke length, wherein the motor foot is movable proximally and in disengagement from the proximal portion of the plunger until the motor toot engages with an interior proximal portion of the drive coupling at which the drive coupling and the syringe coupling together as a unit are moved for an amount of proximal translation to retract the needle inside the device housing.

13. The assembly of claim 9, wherein the syringe coupling comprises a pair of protrusions extending distally within the guide track and configured to receive said protrusion of said drive coupling to lock the syringe coupling to the drive coupling, and, in response to rotation and distal translation of said syringe assembly relative to the drive coupling, said protrusion of said drive coupling is cleared from the guide track of said syringe coupling to allow the syringe assembly to be removed from said assembly.

* * * * *

UNITED STATES PATENT AND TRADEMARK OFFICE
CERTIFICATE OF CORRECTION

| | | |
|---|---|---|
| PATENT NO. | : 11,850,402 B2 | Page 1 of 1 |
| APPLICATION NO. | : 18/004214 | |
| DATED | : December 26, 2023 | |
| INVENTOR(S) | : Kelsey Christine Bayer et al. | |

It is certified that error appears in the above-identified patent and that said Letters Patent is hereby corrected as shown below:

In the Claims

Column 14, Line 36:
In Claim 12, delete "toot" and insert -- foot --

Signed and Sealed this
Twenty-third Day of April, 2024

*Katherine Kelly Vidal*

Katherine Kelly Vidal
*Director of the United States Patent and Trademark Office*